US008840543B2

(12) United States Patent
Deng et al.

(10) Patent No.: US 8,840,543 B2
(45) Date of Patent: Sep. 23, 2014

(54) PARFOCAL COUPLER FOR ENDOSCOPIC VIEWING SYSTEM

(71) Applicants: Wenjie Deng, San Jose, CA (US); Chien Mien Pang, San Jose, CA (US)

(72) Inventors: Wenjie Deng, San Jose, CA (US); Chien Mien Pang, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 62 days.

(21) Appl. No.: 13/664,809

(22) Filed: Oct. 31, 2012

(65) Prior Publication Data

US 2013/0150669 A1 Jun. 13, 2013

Related U.S. Application Data

(60) Provisional application No. 61/567,782, filed on Dec. 7, 2011.

(51) Int. Cl.
*A61B 1/04* (2006.01)
*A61B 1/00* (2006.01)

(52) U.S. Cl.
CPC ............... *A61B 1/00112* (2013.01); *A61B 1/042* (2013.01)
USPC .......................................... 600/112; 600/109

(58) Field of Classification Search
CPC ........................ G02B 23/2438; A61B 1/00188; A61B 1/0019
USPC ............. 600/112, 163, 167; 359/825; 348/75; 396/17
See application file for complete search history.

(56) References Cited

U.S. PATENT DOCUMENTS

| 3,090,282 | A | | 5/1963 | Angenieux |
| 3,765,748 | A | * | 10/1973 | Mito ............................ 359/701 |
| 4,076,018 | A | | 2/1978 | Heckele |
| 4,281,907 | A | | 8/1981 | Kamata |
| 4,380,378 | A | | 4/1983 | Tamura |
| 4,416,513 | A | * | 11/1983 | Uesugi ......................... 359/824 |
| 4,500,181 | A | | 2/1985 | Takahashi |
| 4,558,691 | A | | 12/1985 | Okada |
| 4,569,333 | A | | 2/1986 | Bel et al. |
| 4,611,888 | A | | 9/1986 | Prenovitz et al. |
| 4,639,772 | A | | 1/1987 | Sluyter et al. |
| 4,685,450 | A | | 8/1987 | Collins et al. |
| 4,697,894 | A | | 10/1987 | Takamura et al. |

(Continued)

FOREIGN PATENT DOCUMENTS

DE 1 253 407 11/1967
JP 57-195339 A 12/1982

*Primary Examiner* — Alireza Nia
*Assistant Examiner* — Timothy J Neal
(74) *Attorney, Agent, or Firm* — Flynn, Thiel, Boutell & Tanis, P.C.

(57) ABSTRACT

A coupler for connecting an endoscope to a camera including a cylinder having a zoom lens and a focus lens therein. A zoom adjustment member engages the cylinder with a first coefficient of friction and is movable relative thereto to cause axial movement of the zoom lens. The zoom adjustment member is operatively connected to a focus adjustment member such that movement of the zoom adjustment member causes the focus adjustment member to move thereby moving both the zoom lens and the focus lens axially. The focus adjustment member engages the zoom adjustment member with a second coefficient of friction and is movable relative thereto to cause axial movement of the focus lens within the cylinder. The first coefficient of friction is greater than the second coefficient of friction such that movement of the focus adjustment member does not cause movement of the zoom adjustment member.

25 Claims, 14 Drawing Sheets

(56) References Cited

U.S. PATENT DOCUMENTS

| | | |
|---|---|---|
| 4,740,058 A | 4/1988 | Hori et al. |
| 4,781,448 A | 11/1988 | Chatenever et al. |
| 4,807,594 A | 2/1989 | Chatenever |
| 4,844,071 A | 7/1989 | Chen et al. |
| 4,934,789 A | 6/1990 | Lemke |
| 4,947,245 A | 8/1990 | Ogawa et al. |
| 4,969,450 A | 11/1990 | Chinnock et al. |
| 5,056,902 A | 10/1991 | Chinnock et al. |
| 5,156,141 A | 10/1992 | Krebs et al. |
| 5,212,595 A | 5/1993 | Dennison, Jr. et al. |
| 5,245,475 A | 9/1993 | Takasugi |
| 5,359,992 A | 11/1994 | Hori et al. |
| 5,418,645 A | 5/1995 | Coath et al. |
| 5,575,757 A | 11/1996 | Kennedy et al. |
| 5,630,771 A * | 5/1997 | Weber et al. ............ 475/338 |
| 5,706,143 A | 1/1998 | Hipp |
| 5,707,340 A * | 1/1998 | Hipp et al. ............ 600/112 |
| 5,803,813 A | 9/1998 | Hosdez et al. |
| 5,808,813 A | 9/1998 | Lucey et al. |
| 5,836,867 A | 11/1998 | Speier et al. |
| 5,868,664 A | 2/1999 | Speier et al. |
| 5,978,161 A | 11/1999 | Lemke |
| 6,099,467 A | 8/2000 | Kehr et al. |
| 6,113,533 A | 9/2000 | Howes et al. |
| 6,155,973 A | 12/2000 | Howes et al. |
| 6,522,477 B2 | 2/2003 | Anhalt |
| 6,632,173 B1 | 10/2003 | Kehr et al. |
| 6,633,438 B2 | 10/2003 | Anhalt |
| 2007/0010707 A1 * | 1/2007 | Leiner et al. ............ 600/112 |

\* cited by examiner

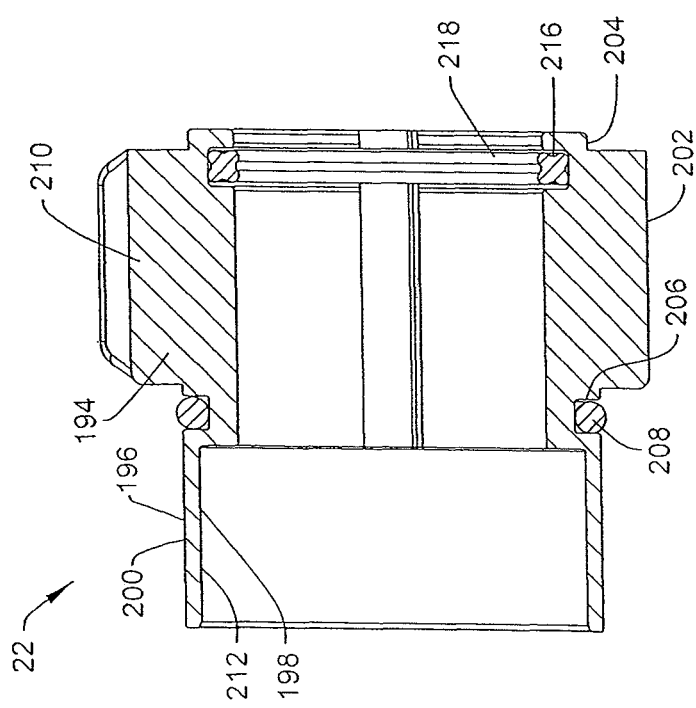

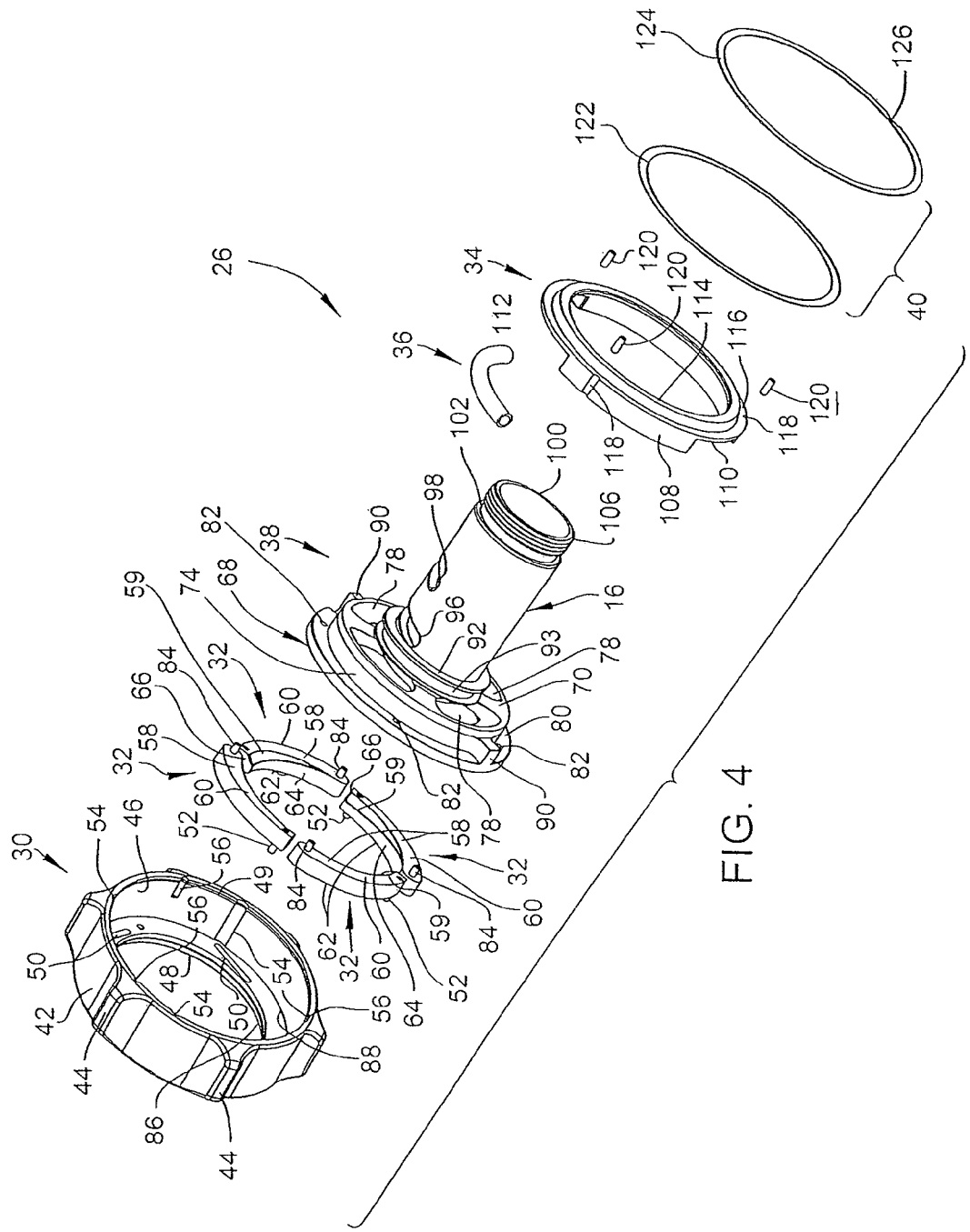

PARFOCAL COUPLER FOR ENDOSCOPIC VIEWING SYSTEM

CROSS REFERENCE TO RELATED APPLICATIONS

This claims the benefit of U.S. Provisional Application No. 61/567 782, filed Dec. 7, 2011, the disclosure of which is hereby incorporated by reference in its entirety.

FIELD OF THE INVENTION

This invention relates generally to endoscopic viewing systems and, more particularly, to a parfocal coupler for use with such systems.

BACKGROUND OF THE INVENTION

Whenever possible, surgeons prefer to perform surgery endoscopically. To perform endoscopic surgery, an endoscope is inserted into the body at the surgical site. The endoscope is an elongated tube that allows a surgeon to view the portion of the body into which it is inserted. Other surgical instruments inserted in the body at the surgical site can be manipulated based on what the surgeon views through the endoscope. The development of endoscopes, as well as their companion instruments, has made it possible to perform minimally invasive surgery. In this type of surgery, the need to make large incisions to gain access to the surgical site has been eliminated. Instead, the surgeon can insert an endoscope and other equipment through small openings in the body, called portals. One advantage of endoscopic surgery is that, since the incisions are smaller, the portions of the body that need to heal after surgery are reduced. Additionally, because less of the internal tissue of the patient is open to the environment, the extent to which the patient's tissues and organs are open to infection is reduced.

Initially, endoscopes included only an eyepiece through which the surgeon could view the surgical site. A modern endoscope system includes a camera assembly that has a camera head attached to the proximal end of the endoscope. A signal processor receives output signals from the camera head. The output signals are converted by the signal processor into electronic signals that are displayed on a monitor. By providing this type of system, the surgeon and other personnel in the operating room can readily view the surgical site by observing the monitor.

Typically, a lens assembly is included in the endoscopic system between the proximal end of the endoscope and the camera head. The lens assembly is fitted in a coupler attached to the proximal end of the endoscope. The lens assembly includes one or more lenses that are moved to focus the image on a transducer internal to the camera head. The lens assembly may also include one or more lenses that are moved to selectively magnify the image.

During a surgical procedure, the surgeon may want to periodically modify the magnification or the field of view of the surgical site that is displayed on the monitor. In order to accomplish this task, it is often necessary for the surgeon or the operating room personnel to alternatively adjust the position of the lenses internal to the coupler and the magnification setting of the video signal processor. The time and concentration required to make these adjustments both lengthens time needed to perform the surgical procedure and diverts attention from the surgical procedure.

Also, sometimes during the course of a surgical procedure, the quality of the image of the surgical site presented by the endoscope system may deteriorate. This may necessitate having to readjust the position of the lenses internal to the coupler and/or the video image processing performed by the camera position. Again, having the surgeon or other surgical personnel perform these tasks can divert attention away from the actual surgical procedure the surgeon is attempting to perform and can lengthen the overall time it takes for the procedure to be performed. This runs contrary to one of the goals of modern surgery, which is to perform the surgical procedure as quickly as possible in order to minimize the amount of time a patient must spend under anesthetic.

SUMMARY OF THE INVENTION

The present invention, according to one aspect, is directed to a parfocal coupler for connecting an endoscope to a camera. The coupler includes a housing assembly configured to be connected to the camera and the endoscope, with the housing assembly including a cylinder mounting at least one zoom lens and at least one focus lens therein, and a zoom adjustment member and a focus adjustment member located outside of the cylinder of the housing assembly. The zoom adjustment member engages the cylinder with a first coefficient of friction and is movable relative thereto to cause axial movement of the at least one zoom lens within the cylinder of the housing assembly. The zoom adjustment member is operatively connected to the focus adjustment member such that movement of the zoom adjustment member causes the focus adjustment member to move, thereby moving both the at least one zoom lens and the at least one focus lens axially within the cylinder. The focus adjustment member engages the zoom adjustment member with a second coefficient of friction and is movable relative thereto to cause axial movement of the at least one focus lens within the cylinder of the housing assembly. The first coefficient of friction is greater than the second coefficient of friction such that movement of the focus adjustment member does not cause movement of the zoom adjustment member.

Another aspect of the present invention is directed to a coupler for connecting an endoscope to a camera, having a housing configured to be connected to the camera and the endoscope, with the housing assembly having at least one zoom lens and at least one focus lens therein, a zoom adjustment member located outside of the housing, with the zoom adjustment member engaging the housing with a first coefficient of friction and being movable relative thereto to cause axial movement of the at least one zoom lens within the housing, and a focus adjustment member located outside of the housing. The focus adjustment member includes an inner magnetic ring and an outer magnetic ring, wherein the zoom adjustment member is located between the inner magnetic ring and the outer magnetic ring. The outer magnetic ring is magnetically coupled to the inner magnetic ring. The outer magnetic ring engages the zoom adjustment member with a second coefficient of friction such that movement of the zoom adjustment member causes the outer magnetic ring to move thereby moving both the at least one zoom lens and the at least one focus lens within the housing. The first coefficient of friction is greater than the second coefficient of friction such that movement of the outer magnetic ring does not cause movement of the zoom adjustment member.

These and other aspects, objects, and features of the present invention will be understood and appreciated by those skilled in the art upon studying the following specification, claims, and appended drawings.

BRIEF DESCRIPTION OF DRAWINGS

FIG. 3D is a longitudinal cross-sectional view of a zoom adjustment member of the coupler of the present invention.

FIG. 4 is an exploded perspective side view of the endoscope coupler of FIG. 3A.

DETAILED DESCRIPTION OF PREFERRED EMBODIMENTS

For purposes of description herein, it is to be understood that the invention may assume various alternative orientations, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
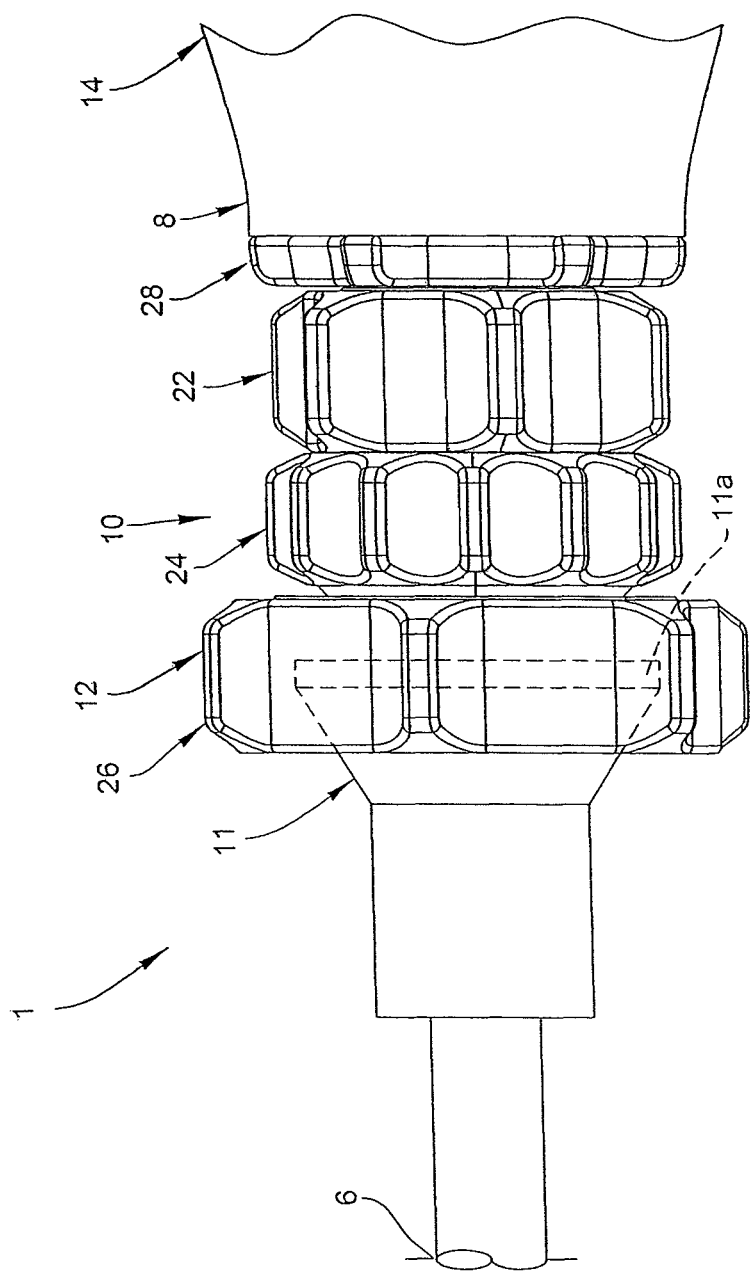
FIG. 1 is a fragmentary side view of an endoscopic viewing system of the present invention.
Figure 2:
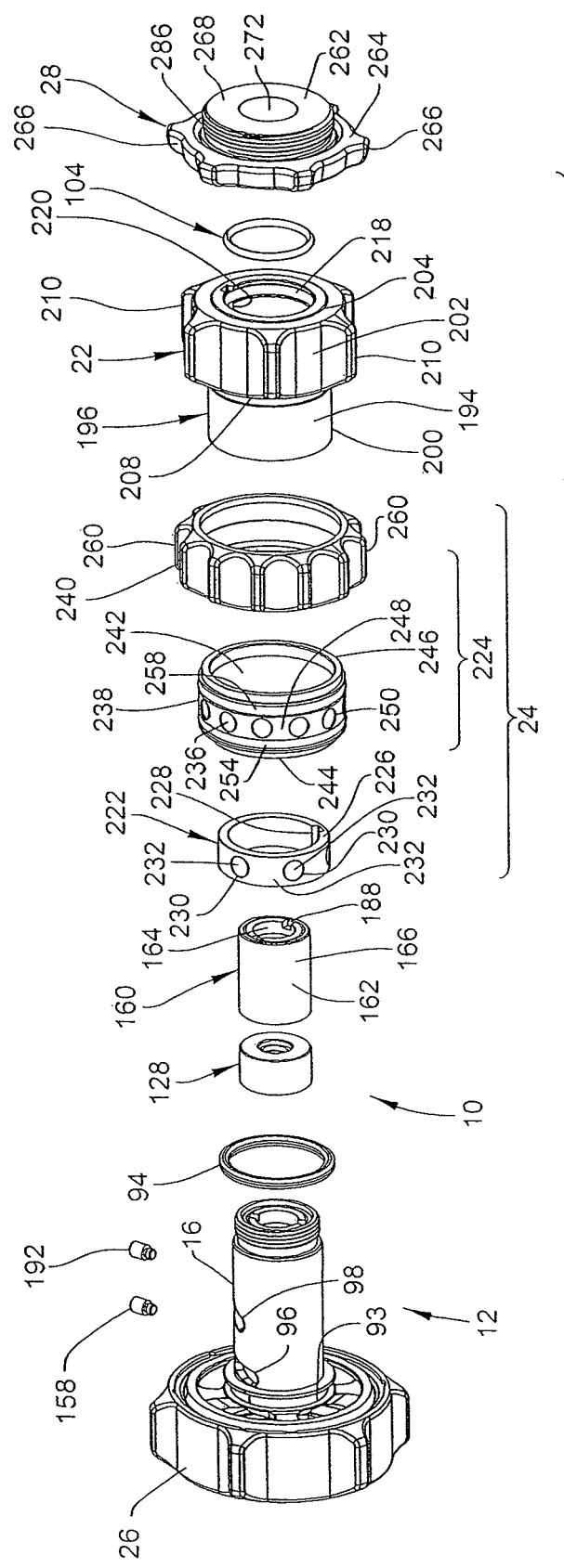
FIG. 2 is an exploded perspective view of a parfocal coupler of the present invention.
Figure 3:
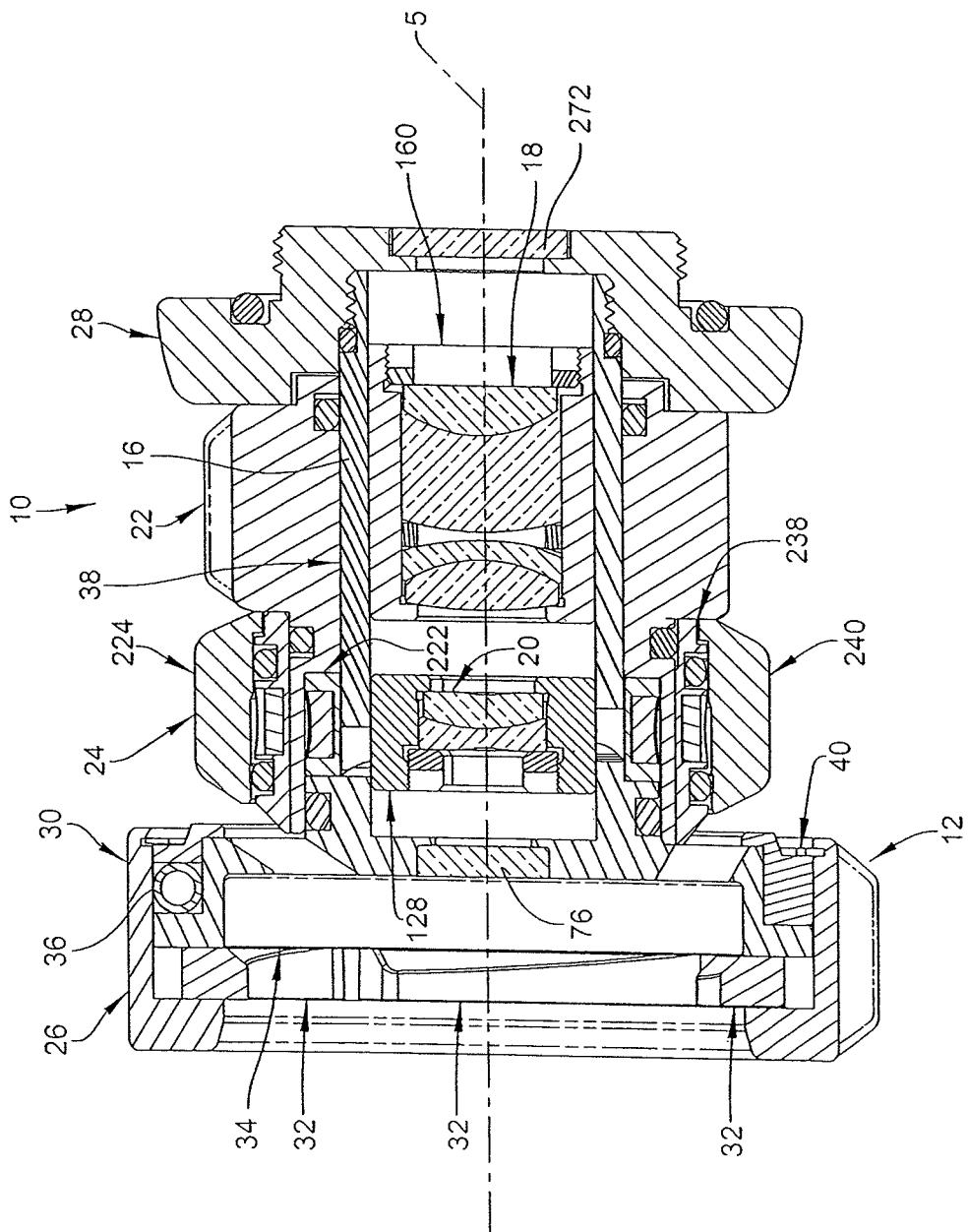
FIG. 3 is a cross-sectional view of the coupler of the present invention, as seen generally along a central longitudinal axis of the coupler.

Referring to FIG. 1 there is illustrated an endoscopic viewing system 1 according to the present invention. The endoscopic viewing system 1 includes an endoscope 11 and a camera 14, with a parfocal coupler 10 located therebetween. The endoscope 11 is inserted in the body through a portal 6. The camera 14 includes a camera head 8 that is physically attached to the coupler 10. Certain terminology will be used in the following description for convenience in reference only, and will not be limiting. For example, the words "axial" and "axially" will mean generally parallel to a central axis 5 of the coupler 10 as illustrated in FIG. 3 and "radial" and "radially" will mean generally in a direction perpendicular to the central axis 5. The words "distal" and "distally" will refer to the direction toward the end of the coupler which is connected to the endoscope 11 and that is closest to the patient, and the words "proximal" and "proximally" will refer to the direction toward the end of the coupler which is connected to the camera 14 and that is furthest from the patient. In FIGS. 1-5, the distal side is a left side of the drawing and a proximal side is a right side of the drawing. Said terminology will include the words specifically mentioned, derivatives thereof, and words of similar import.

The reference number 10 (FIGS. 1-3) generally designates the parfocal coupler embodying the present invention. In the illustrated example, the coupler 10 is for connecting the endoscope 11 to the camera 14. The coupler 10 includes a housing assembly 12 configured to be connected to the camera 14 and the endoscope 11. The housing assembly 12 includes a cylinder 16 having at least one zoom lens 18 and at least one focus lens 20 therein. A zoom adjustment member 22 is located outside of the cylinder 16 of the housing assembly 12. The zoom adjustment member 22 engages the cylinder 16 with a first coefficient of friction. A focus adjustment member 24 is also located outside of the cylinder 16 of the housing assembly 12 axially adjacent the zoom adjustment member 22. The focus adjustment member 24 engages the zoom adjustment member 22 with a second coefficient of friction. Movement of the zoom adjustment member 22 causes the zoom lens 18 to move axially within the cylinder 16 of the housing assembly 12. Likewise, movement of the focus adjustment member 24 causes the focus lens 20 to move axially within the cylinder 16 of the housing assembly 12. Movement of the zoom adjustment member 22 also causes the focus adjustment member 24 to move, thereby moving both the zoom lens 18 and the focus lens 20 axially within the cylinder 16. The first coefficient of friction is greater than the second coefficient of friction such that movement of the focus adjustment member 24 does not cause movement of the zoom adjustment member 22.

In the illustrated example, the housing assembly 12 is configured to be connected to the camera 14 and the endoscope 11 and to house the zoom lens 18 and focus lens 20 within the cylinder 16. The housing assembly 12 includes an endoscope connector 26 including the cylinder 16 with the zoom lens 28 and the focus lens 20 therein and a camera adapter 28, with the zoom adjustment member 22 and the focus adjustment member 24 being captured between the endoscope connector 26 and the camera adapter 28.

The illustrated endoscope connector 26 (FIGS. 3, 3A and 4) is configured to be connected to the endoscope 11 and includes the zoom lens 18 and focus lens 20 therein. The endoscope connector 26 includes an end ring member 30, a plurality of connection wedges 32, a stop ring 34, a compression spring 36, a cylinder member 38 including the cylinder 16 and a holding disc assembly 40. The end ring member 30 comprises an outer ring 42 having a plurality of grip ridges 44 extending radially from an outer surface thereof for providing a grip engagement for allowing the end ring member 30 to be easily rotated. An interior of the outer ring 42 is defined by an interior cylindrical surface 46 and an inwardly extending circular lip 48 at the distal end of the interior cylindrical surface 46 adjacent the endoscope 11 when the coupler 11 is connected to the endoscope 11. The interior cylindrical surface 46 of the outer ring 42 also includes a holder channel 49 extending circumferentially about the interior cylindrical surface 46 adjacent a proximal side thereof. As illustrated in FIG. 4, the interior cylindrical surface 46 includes a plurality of circumferentially spaced and parallel, inwardly opening longer channels 54 extending from the proximal end of the outer ring 42 to the inwardly extending lip 48 and a plurality of circumferentially spaced and parallel, inwardly opening shorter channels 56 extending from the proximal end of the outer ring 42. Both the longer channels 54 and the shorter channels 56 extend axially to and communicate with the holder channel 49. A surface of the inwardly extending lip 48 facing inwardly and axially towards the proximal end of the outer ring 42 includes a plurality of pin slots 50 arranged about the inwardly extending lip 48 in circumferentially spaced relation with one another and opening axially inwardly towards the proximal end of the outer ring 42 and the wedges 32 (see FIG. 4). As discussed in more detail below, the pin slots 50 cooperate with the wedges 32 to help move the wedges 32, and in the illustrated embodiment, the number of pin slots 50 is identical to the number of wedges 32. Specifically, in the illustrated example, four linear pin slots 50 are shown for use with four wedges 32. However, it is contemplated that any number of wedges 32 and pin slots 50 could be used (depending on the number of wedges 32) and that the pin slots 50 could be curved.

In the illustrated example, the pin slots 50 on the inwardly extending lip 48 of outer ring 42 are configured to have first pins 52 extending from the wedges 32 inserted therein for allowing the wedges 32 to be moved as the coupler 10 is connected and disconnected to the endoscope 11. The wedges 32 each comprise an arcuate body 58 extending approximately 80° of a circle. The body 58 has a substantially planar top surface 60 and bottom surface 62, with a top angled portion 59 extending from an interior face 64 to the top surface 60. Each wedge 32 includes the first pins 52 extending from the bottom surface 62 adjacent a first end 66 of the wedges 32 and into one of the pin slots 50 on the inwardly extending lip 48 of the outer ring 42. To be discussed in more detail below, the first end 66 of the wedge 32 having the first pin 52 adjacent thereto moves outward as the first pin 52 slides along the pin slot 50 from an end of the pin slot 50 adjacent an inner periphery 86 of the inwardly extending lip 48 towards an outer periphery 88 of the inwardly extending lip 48 (i.e., where the inwardly extending lip 48 intersects the interior cylindrical surface 46 of the outer ring 42 of the end ring member 30).

Figure 3A:
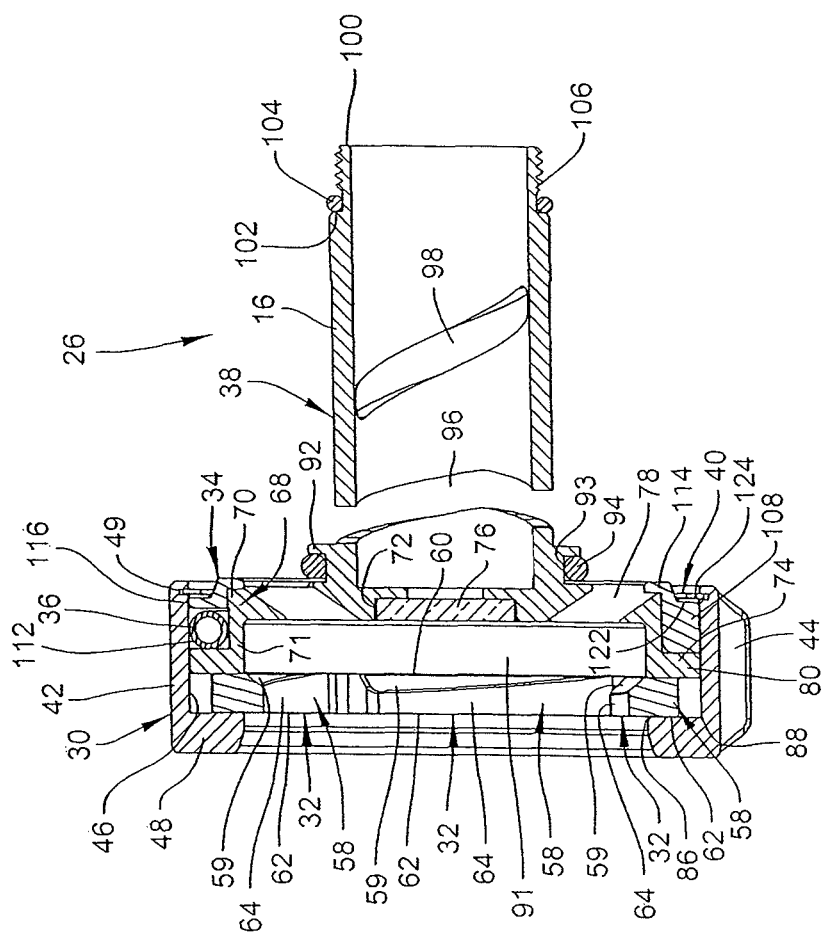
FIG. 3A is a longitudinal cross-sectional view of an endoscope coupler of the coupler of the present invention.

The illustrated cylinder member 38 sits on the wedges 32 and assists in moving the first end 66 of the wedges 32 outward. The cylinder member 38 includes a base 68 and the cylinder 16. The base 68 includes a plate 70 having a central opening 72 (see FIG. 3A) and an L-shaped ring 74 depending from a distal side of the plate 70 towards the wedges 32 and the inwardly extending lip 48 of the outer ring 42 of the end ring member 30 when the endoscope connector 26 is assembled. The cylinder 16 extends axially from a proximal side of the plate 70 outside of the central opening 72 as illustrated in FIG. 3A. The central opening 72 seats a first transparent glass disc 76 therein. The first transparent glass disc 76 is located within the central opening 72 (e.g., by an interference fit and/or with an adhesive) and allows the image taken by the endoscope 11 to pass therethrough without modifying or altering the image (i.e., the first transparent glass disc 76 is not a lens in the present example (although it is contemplated that the disc 76 could be a lens working to magnify or focus the image)). The plate 70 has a plurality of oblique apertures 78 therethrough. The L-shaped ring 74 includes a circular leg 71 extending axially from an outside periphery of the distal side of the plate 70 and a circular foot 80 extending radially outward from a terminal distal end of the circular leg 71. The circular foot 80 is configured to rest on the wedges 32. As illustrated in FIG. 4, the circular foot 80 includes a plurality of circumferentially spaced and axially extending holes 82 configured to receive second pins 84 extending from a proximal side of the wedges 32 facing the circular foot 80.

In the illustrated example, the cylinder member 38 rotates relative to the end ring member 30 to assist in connecting the coupler 10 to the endoscope 11. As illustrated in FIG. 4, the circular foot 80 of the L-shaped ring 74 of the base 68 of the cylinder member 38 has a circular periphery. Therefore, when the cylinder member 38 is rotated relative to the end ring member 30, the holes 82 and the second pins 84 therein move along an arc of constant radius. Rotation of the cylinder member 38 relative to the end ring member 30 thereby causes the wedges 32 to move in the same direction of rotation of the cylinder member 38. As described in more detail below, the cylinder member 38 is biased to a position wherein the first pins 52 at the first end 66 of the wedges 32 are within the pin slots 50 at a position adjacent the inner periphery 86 of the inwardly extending lip 48 of the end ring member 30. When the cylinder member 38 is rotated against the bias, the second pins 84 within the circular foot 80 of the L-shaped ring 74 of the base 68 cause the wedges 32 to move and push the first pins 52 along the pin slots 50 towards the outer periphery 88 of the inwardly extending lip 48 of the end ring member 30. Once the cylinder member 38 is fully rotated, the interior face 64 of the wedges 32 will be aligned with the inner periphery 86 of the inwardly extending lip 48 of the end ring member 30, thereby placing the coupler 10 in a receiving position. When the coupler 10 is in the receiving position, the endoscope 11 can be inserted into the endoscope connector 26 without interference from the wedges 32. The cylinder member 38 can then be released to force the cylinder member 38 to rotate in an opposite direction to move the second pins 84 within the circular foot 80 of the L-shaped ring 74 of the base 68 to cause the wedges 32 to move and pull the first pins 52 along the pin slots 50 towards the inner periphery 86 of the inwardly extending lip 48 of the end ring member 30. Once the cylinder member 38 is fully rotated back to its original position, the interior face 64 of the wedges 32 will cover an annular connection flange 11a (see FIG. 1) of the endoscope 11, and capture the annular connection flange 11a in a capture space 91 axially located between the wedges 32 and a bottom surface of the circular foot 80 of the L-shaped ring 74 of the base 68 of the cylinder member 38, to thereby connect the endoscope 11 to the coupler 10 in a locked position. The top angled portions 59 of the wedges 32 assist in allowing the first end 66 of the wedges 32 to move inward under the annular connection flange of the endoscope 11.

In the illustrated embodiment, the L-shaped ring 74 includes a pair of stop blocks 90. The stop blocks 90 are connected to the L-shaped ring 74 at circumferentially spaced locations. Each stop block 90 is connected to the circular leg 71 and the circular foot 80 and extends radially outward from an outer surface of the circular leg 71 and extends axially in a proximal direction from a proximal surface the circular foot 80 facing away from the wedges 32. The stop blocks 90 are used to limit the range of rotation of the cylinder member 38 relative to the end ring member 30 and to bias the cylinder member 38 to the locked position wherein the wedges 32 extend beyond the inner periphery 86 of the of the inwardly extending lip 48 of the end ring member 30.

The illustrated stop ring 34 and compression spring 36 cover the base 68 of the cylinder member 38 to control rotation of the cylinder member 38 (see FIGS. 3, 3A and 4). The stop ring 34 includes a disc 108 having a shorter cut-out portion 110 and an opposite longer cut-out portion 112 in a distal surface thereof facing the wedges 32. A bent circular ridge 114 extends axially and radially from a proximal surface of the disc 108 at an inner periphery thereof and defines a circular receiving face 116 on the disc 108 radially outside of the bent circular ridge 114. An outside periphery of the disc 108 includes a plurality of grooves 118 opening radially outward. The stop ring 34 is connected to the end ring member 30 by placing the stop ring 34 over the base 68 of the cylinder member 38 along an axial direction towards a distal end of the stop ring 34, with the grooves 118 on the outside periphery of the disc 108 being aligned with the shorter channels 56 in the interior cylindrical surface 46 of the outer ring 42 of the end ring member 30. Stop pins 120 are inserted into the space defined by the grooves 118 on the outside periphery of the disc 108 and the shorter channels 56 in the interior cylindrical surface 46 of the outer ring 42 of the end ring member 30, thereby preventing the stop ring 34 from rotating relative to the end ring member 30.

In the illustrated embodiment, a first one of the stop blocks 90 of the base 68 of the cylinder member 38 is located within the shorter cut-out portion 110 of the disc 108 of the stop ring 34. The circumferential distance of the shorter cut-out portion 110 defines the distance of travel of the cylinder member 38 relative to the end ring member 30 as the stop bock 90 within the short cut-out portion 110 will abut against the disc 108 at ends of the short cut-out portion 110 during rotation of the cylinder member 38. A second one of the stop blocks 90 of the base 68 of the cylinder member 38 is located within the longer cut-out portion 112 of the disc 108 of the stop ring 34. The compression spring 36 is positioned within the longer cut-out portion 112 of the disc 108 of the stop ring 34 between one end wall of the long cut-out portion 112 and the second one of the stop blocks 90.

In the illustrated example, the compression spring 36 biases the stop blocks 90 of the base 68 of the cylinder member 38 to a position wherein the wedges 32 extend beyond the inner periphery 86 of the inwardly extending lip 48 of the end ring member 30. When the cylinder member 38 is rotated relative to the end ring member 30, the compression spring 36 is compressed between the stop block 90 of the base 68 within the longer cut-out portion 112 of the stop ring 34 and the one end wall of the long cut-out portion 112. When the compression spring 36 is compressed, the coupler 10 is in the receiving position. Once one of the cylinder member 38 and the end ring member 30 is released, the compression spring 36 will expand to force the cylinder member 38 to rotate, thereby forcing the wedges 32 outward into the locked position.

The illustrated wedges 32, cylinder member 38, compression spring 36 and stop ring 34 are maintained within the end ring member 30 by the holding disc assembly 40 (see FIGS. 3, 3A and 4). The holding disc assembly 40 includes a unitary ring disc 122 and a split ring disc 124. The unitary ring disc 122 is positioned on the receiving face 116 of the disc 108 of the stop ring 34. The split ring disc 124 is positioned over the unitary ring disc 122 to capture the unitary ring disc 122 between the split ring disc 124 and the receiving face 116 of the disc 108 of the stop ring 34. The split ring disc 124 includes a split 126 to allow the diameter of the split ring disc 124 to be temporarily reduced to allow the split ring disc 124 to be positioned over the unitary ring disc 112 and then expanded radially to fit within the holder channel 49 extending about the interior cylindrical surface 46 of the outer ring 42 of the end ring member 30, thereby forming the endoscope connector 26.

In the illustrated example, the cylinder 16 of the cylinder member 38 is configured to engage the camera adapter 28 and house the zoom lens 18 and the focus lens 20 therein. The cylinder member 38 includes an annular flange 92 extending around the circumference of the distal end of the cylinder 16 adjacent the plate 70 of the base 68. The annular flange 92 and the proximal surface of the plate 70 define an outwardly facing O-ring track 93 having a first O-ring 94 (not illustrated in FIG. 4) therein. The cylinder member 38 also includes a substantially chevron-shaped focus cut-out track 96 and a helical-shaped zoom cut-out track 98. As discussed in more detail below, the substantially chevron-shaped focus cut-out track 96 defines a path of movement of the focus lens 20 and the helical-shaped zoom cut-out track 98 defines a path of movement of the zoom lens 18. The cylinder 16 includes a ledge 102 adjacent a proximal end 100 thereof forming a seat for a second O-ring 104. An outside surface of the cylinder 16 between the ledge 102 and the proximal end 100 thereof includes external threads 106 for connecting the endoscope connector 26 to the camera adapter 28. The focus lens 20 and the zoom lens 18 are located within the cylinder 16 of the cylinder member 38.

Figure 3B:
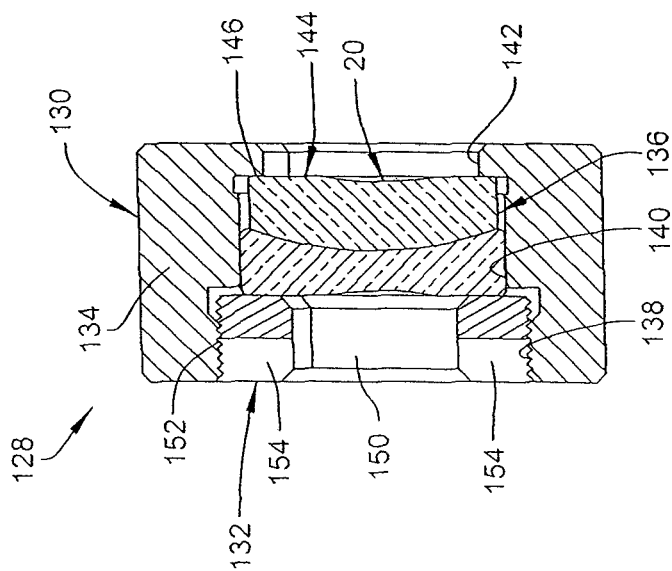
FIG. 3B is a longitudinal cross-sectional view of a focus lens holder assembly of the coupler of the present invention.
Figure 6:
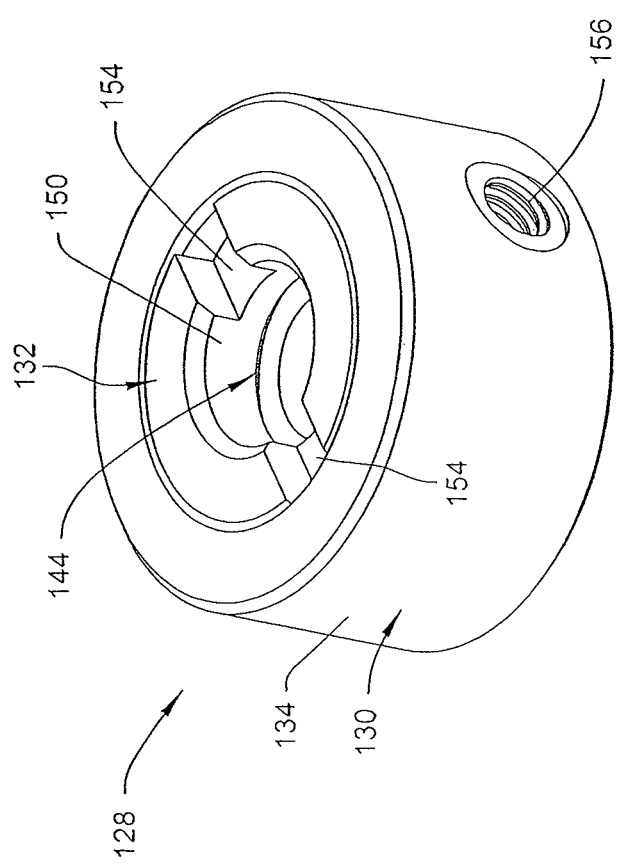
FIG. 6 is a perspective view of the focus lens holder assembly of the present invention.

The illustrated focus lens 20 is used to focus the image taken by the endoscope 11. The focus lens 20 is located in a focus lens holder assembly 128 (FIGS. 3, 3B and 6). The focus lens holder assembly 128 includes a focus lens holder 130 and a cap 132. The focus lens holder 130 includes a cylinder 134 having a stepped interior 136 defining a larger diameter threaded distal first area 138, a middle diameter second area 140 and a smaller diameter proximal third area 142. The focus lens 20 in the illustrated embodiment includes a focus lens pair 144 located within the middle diameter second area 140 and abutting a step 146 between the middle diameter second area 140 and the smaller diameter proximal third area 142. The cap 132 has a central opening 150 and an outside threaded surface 152 that engages with the larger diameter threaded distal first area 138 of the stepped interior 136 of the cylinder 134 to lock the focus lens 20 within the cylinder 134. The cap 132 has a pair of radially extending screw grooves 154 that are radially aligned with one another on opposite sides of the central opening 150 and open in a distal direction, with the screw grooves 154 being configured to receive a flat screwdriver head therein for allowing the cap 132 to easily rotated and threaded into the focus lens holder 130.

Figure 5:
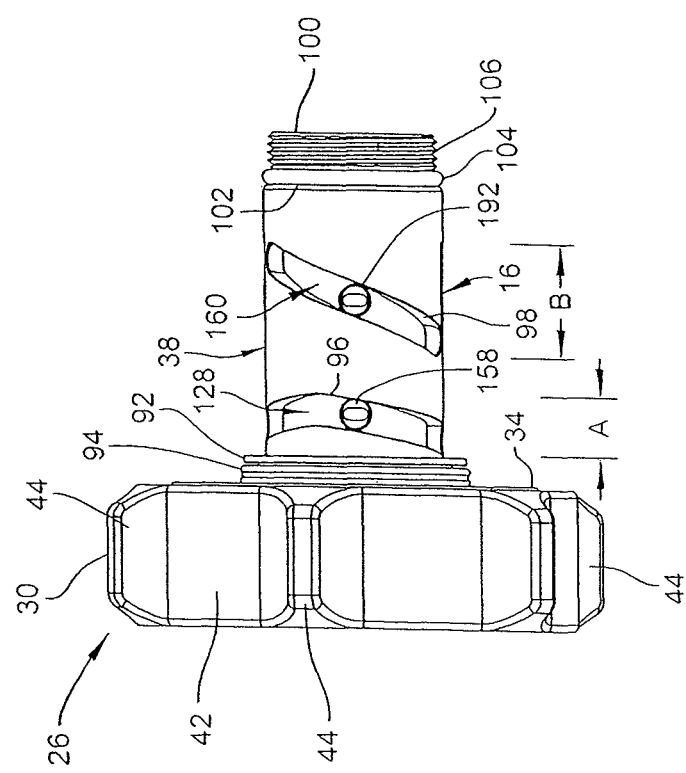
FIG. 5 is a side view of the endoscope coupler of the coupler of the present invention.

The focus lens holder 130 includes a radially extending threaded hole 156 into the outside surface of the cylinder 134 for receipt of a first threaded pin 158. The threaded hole 156 can be a blind hole or can extend into the stepped interior 136 of the cylinder 134. As illustrated in FIG. 5, the first threaded pin 158 extends through the focus cut-out track 96 in the cylinder 16 of the cylinder member 38. As described in more detail below, as the first threaded pin 158 moves along the focus cut-out track 96 in the cylinder 16 of the cylinder member 38, the focus lens holder assembly 128 with the focus lens 20 therein moves axially along the cylinder 16 to adjust the focus of the image passing through the coupler 10.

Figure 3C:
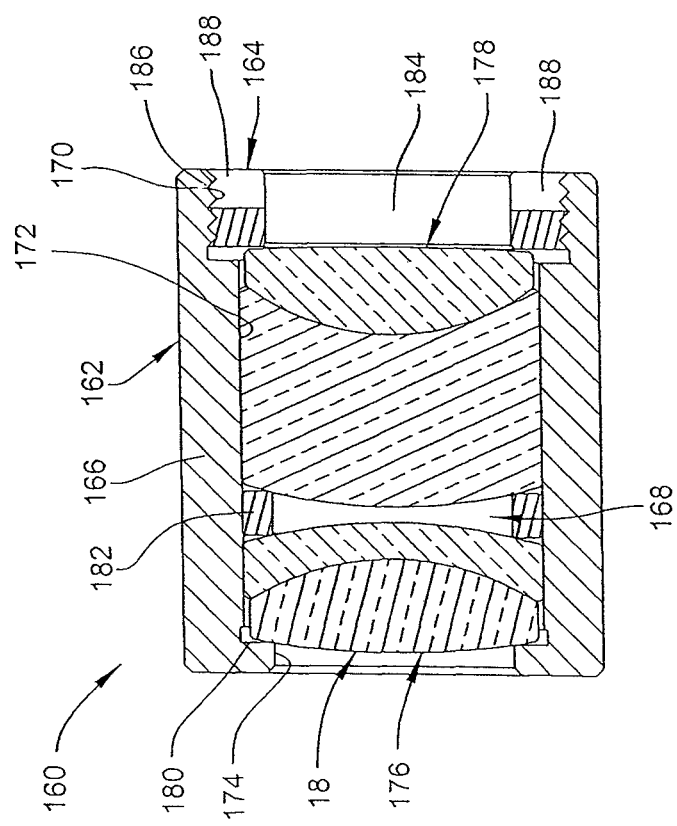
FIG. 3C is a longitudinal cross-sectional view of a zoom lens holder assembly of the coupler of the present invention.
Figure 7:
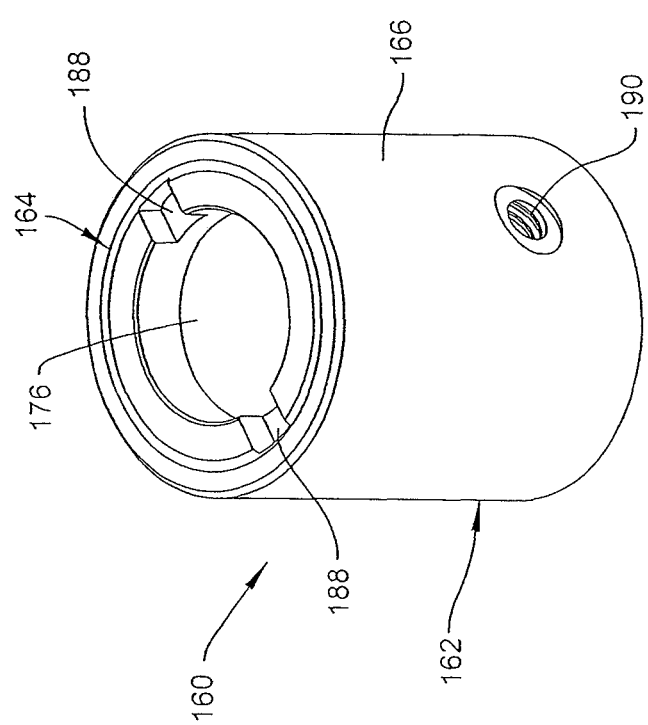
FIG. 7 is a perspective view of the zoom lens holder assembly of the present invention.

In the illustrated example, the zoom lens 18 is used to magnify the image taken by the endoscope 11. The zoom lens 18 is located in a zoom lens holder assembly 160 (FIGS. 3, 3C and 7). The zoom lens holder assembly 160 includes a zoom lens holder 162 and a cap 164. The zoom lens holder 162 includes a cylinder 166 having a stepped interior 168 defining a larger diameter threaded proximal first area 170, a middle diameter second area 172 and a smaller diameter distal third area 174. The zoom lens 18, in the illustrated embodiment, includes a first zoom lens pair 176 and a second zoom lens pair 178 located within the middle diameter second area 172. The first zoom lens pair 176 abuts a step 180 located between the middle diameter second area 172 and the smaller diameter distal third area 174. A spacer ring 182 is axially located between the first zoom lens pair 176 and the second zoom lens pair 178 within the middle diameter second area 172 of the stepped interior 168 of the cylinder 166 of the zoom lens holder 162. The cap 164 has a central opening 184 and an outside threaded surface 186 that engages with the larger diameter threaded proximal first area 170 of the stepped interior 168 of the cylinder 166 to lock the zoom lens 18 within the cylinder 166. The cap 164 has a pair of radially extending screw grooves 188 that are radially aligned with one another on opposite sides of the central opening 184 and opening in a proximal direction, with the screw grooves 188 being configured to receive a flat screwdriver head therein for allowing the cap 164 to easily rotated and threaded into the focus lens holder 162.

The zoom lens holder 162 includes a radially extending threaded hole 190 which opens at the outside surface of the cylinder 166 for receipt of a second threaded pin 192. As illustrated in FIG. 5, the second threaded pin 192 extends through the zoom cut-out track 98 in the cylinder 16 of the cylinder member 38. As described in more detail below, as the second threaded pin 192 moves along the zoom cut-out track 98 in the cylinder 16 of the cylinder member 38, the zoom lens holder assembly 160 with the zoom lens 18 therein moves axially along the cylinder 16 to magnify the image passing through the coupler 10.

The illustrated zoom adjustment member 22 interacts with the second threaded pin 192 to move the zoom lens 18 within the cylinder 16. As illustrated in FIG. 3D, the zoom adjustment member 22 includes a tube 194 having a stepped exterior surface 196 and a stepped interior surface 198. The stepped exterior surface 196 includes a smaller diameter distal side portion 200, a larger diameter middle portion 202, and a smaller diameter proximal side portion 204. A radially outwardly opening O-ring groove 206 having a third O-ring 208 therein is located between the smaller diameter distal side portion 200 and the larger diameter middle portion 202. The larger diameter middle portion 202 includes a plurality of grip ridges 210 extending radially outward for allowing the zoom adjustment member 22 to be easily grasped and rotated. The stepped interior surface 198 includes a distal side larger diameter area 212 and a proximal side smaller diameter area 214. As illustrated in FIG. 3, the proximal side smaller diameter area 214 includes an inwardly radially facing circumferential inner O-ring channel 216 housing a fourth O-ring 218 therein. As illustrated in FIGS. 2 and 3D, the proximal side smaller diameter area 214 includes an axial groove 220 configured to receive the second threaded pin 192 therein.

Figure 3E:
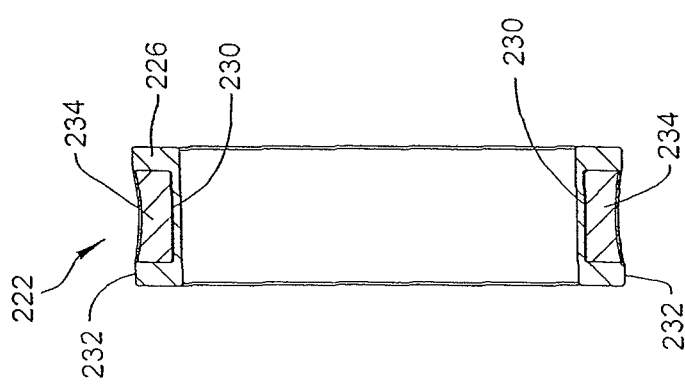
FIG. 3E is a longitudinal cross-sectional view of an inner magnet ring of a focus adjustment member of the coupler of the present invention.
Figure 3F:
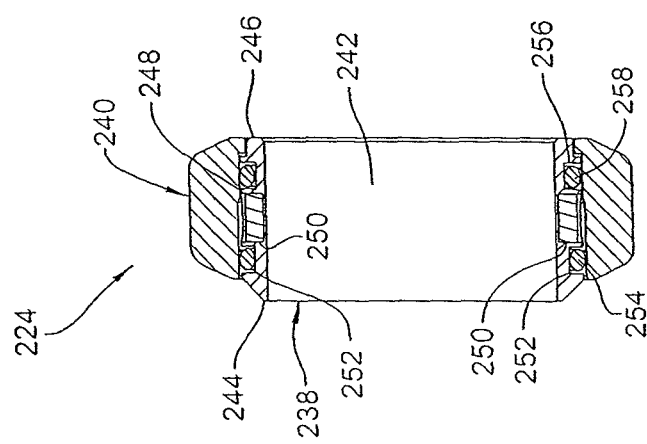
FIG. 3F is a longitudinal cross-sectional view of an outer focus ring assembly of the focus adjustment member of the coupler of the present invention.

In the illustrated example, the focus adjustment member 24 interacts with the first threaded pin 158 to move the focus lens 20 within the cylinder 16. The focus adjustment member 24 includes an inner magnet ring 222 (FIGS. 2, 3 and 3E) and an outer focus ring assembly 224 (FIGS. 2, 3 and 3F) located radially outside of the inner magnet ring 222. The inner magnet ring 222 includes a tube 226 having an inner surface with an axial groove 228 opening radially inward (see FIG. 2) and a plurality of first magnet pockets 230 opening radially outward at an exterior surface 232. The first magnet pockets 230 each hold a first magnet 234 therein. The first magnets 234 within the first magnet pockets 230 interact with second magnets 236 within the outer focus ring assembly 224 such that rotation of the outer focus ring assembly 224 also rotates the inner magnet ring 222.

The illustrated outer focus ring assembly 224 includes an inner magnet band 238 and an outer ring 240. The inner magnet band 238 comprises a smooth inner surface 242, a distal side edge 244, a proximal side edge 246 and a radially outer surface 248. The outer surface 248 of the inner magnet band 238 includes a plurality of second magnet pockets 250 opening radially outwardly and arranged in a ring about a circumference of the inner magnet band 238. The second magnet pockets 250 of the inner magnet band 238 are axially surrounded by a distal O-ring channel 252 having a first focus O-ring 254 therein and a proximal O-ring channel 256 having a second focus O-ring 258 therein. In the illustrated embodiment, the distal side edge 244 defines a point for minimizing contact between the outer focus ring assembly 224 and the endoscope connector 26 for allowing the focus adjustment member 24 to easily rotate as described in more detail below.

The outer ring 240 of the outer focus ring assembly 224 includes a plurality of grip ridges 260 extending radially outward from an outer surface thereof for allowing the outer ring 240 to be easily gripped and rotated. The inner magnet band 238 is inserted into the outer ring 240 with an interference fit to connect the inner magnet band 238 to the outer ring 240.

Figure 3G:
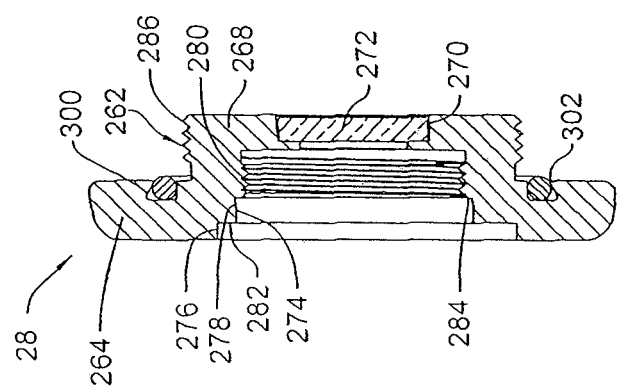
FIG. 3G is a longitudinal cross-sectional view of a camera coupler of the coupler of the present invention.

In the illustrated example, the camera adapter 28 (FIGS. 2, 3 and 3G) is connected to the endoscope connector 26 to capture the zoom adjustment member 22 and the focus adjustment member 24 between the camera adapter 28 and the endoscope connector 26. The camera adapter 28 includes an externally threaded cylinder 262 including a distal grip extension 264 having a plurality of grip ridges 266 extending radially outward at a distal end thereof and an inwardly extending disc-shaped flange 268 at a proximal end thereof. The inwardly extending disc-shaped flange 268 is configured to be received within the camera 14 when the camera adapter 28 is connected to the camera 14. The grip extension 264 has a circular O-ring channel 300 opening in a proximal direction and facing the camera head 8 when the camera 14 is connected to the camera adapter 28. The O-ring channel 300 houses a fifth O-ring 302 therein for creating a seal between the camera adapter 28 and the camera head 8 when the camera head 8 is screwed onto the camera adapter 28. The inwardly extending disc-shaped flange 268 includes a recess 270 housing a second transparent glass disc 272 therein. The second transparent glass disc 272 is located within the recess 270 (e.g., by an interference fit and/or with an adhesive) and allows the image taken by the endoscope 11 to pass therethrough without modifying or altering the image (i.e., the second transparent glass disc 272 is not a lens in the present example (although it is contemplated that the disc 272 could be a lens working to magnify or focus the image)). The externally threaded cylinder 262 includes a stepped interior bore 274 having a distal end larger diameter area 276, a middle area 278 and a proximal end smaller diameter area 280. A zoom ring abutment step 282 is located between the distal end larger diameter area 276 and the middle area 278 and an O-ring abutment step 284 is located between the middle area 278 and the proximal end smaller diameter area 280.

The illustrated coupler 10 is assembled by inserting the focus lens holder assembly 128 and the zoom lens holder assembly 160 within the cylinder 16 of the cylinder member 38 of the endoscope connector 26 from the proximal end 100 thereof. As shown in FIG. 5, the first threaded pin 158 extends radially through the focus cut-out track 96 and the second threaded pin 192 extends radially through the zoom cut-out track 98 in the cylinder 16 of the cylinder member 38 of the endoscope connector 26 of the coupler 10. The inner magnet ring 222 of the focus adjustment member 24 is then slid axially onto the cylinder 16 of the cylinder member 38 of the endoscope connector 26 from the proximal end 100 thereof. As the inner magnet ring 222 is slid axially onto the cylinder 16, the second threaded pin 192 slides axially fully through the inner axial groove 228 of the tube 226 of the inner magnet ring 222. Thereafter, the first threaded pin 158 is axially slid partially through the inner axial groove 228 until the tube 226 of the inner magnet ring 222 abuts against the annular flange 92 of the cylinder member 38 as illustrated in FIG. 3. The inner axial groove 228 of the tube 226 of the inner magnet ring 222 is longer than an axial movement distance A of the first threaded pin 158 (see FIG. 5) such that the first threaded pin 158 will always be located within the inner axial groove 228 of the tube 226 of the inner magnet ring 222 as long as the tube 226 of the inner magnet ring 222 abuts the annular flange 92 of the cylinder member 38, regardless of a position of the first threaded pin 158 within the focus cut-out track 96.

In the illustrated example, the outer focus ring assembly 224 axially is slid onto the smaller diameter distal first side portion 200 of the stepped exterior surface 196 of the zoom adjustment member 22 until the proximal side edge 246 of the inner magnet band 238 abuts against the larger diameter middle portion 202 of the tube 194 of the zoom adjustment member 22 (see FIG. 3). The zoom adjustment member 22 with the outer focus ring assembly 224 thereon is then axially slid over the cylinder 16 of cylinder member 38 until the distal side edge 244 of the inner magnet band 238 and a distal side edge of the zoom adjustment member 22 abuts the plate 70 of the base 68 of the cylinder member 38. As illustrated in FIG. 3, the zoom adjustment member 22 with the outer focus ring assembly 224 thereon is axially slid over the inner magnet ring 222 of the focus adjustment member 24, with the inner magnet ring 222 being captured between the cylinder 16 of the cylinder member 38 and the distal side larger diameter area 212 of the stepped interior surface 198 of the zoom adjustment member 22. As the zoom adjustment member 22 with the outer focus ring assembly 224 thereon is axially slid over the cylinder 16 of cylinder member 38, the second threaded pin 192 axially slides into the axial groove 220 in the proximal side smaller diameter area 214 of the stepped interior surface 198 of the tube 194 of the zoom adjustment member 22. The axial groove 220 of the zoom adjustment member 22 is longer than a axial movement distance B of the second threaded pin 192 (see FIG. 5) such that the second threaded pin 192 will always be located within the axial groove 220 of the zoom adjustment member 22 as long as the zoom adjustment member 22 abuts the plate 70 of the base 68 of the cylinder member 38, regardless of a position of the second threaded pin 192 within the zoom cut-out track 98.

The illustrated coupler 10 is assembled by screwing the camera adapter 28 onto the endoscope connector 26. As illustrated in FIG. 3, the camera adapter 28 is screwed in an axial direction onto the endoscope connector 26 by engaging the threads 106 at the proximal end 100 of the cylinder 16 of the cylinder member 38 with threads 286 on the distal end smaller diameter area 280 of the stepped interior bore 274 of the externally threaded cylinder 262 of the camera adapter 28. It is contemplated that the threads 106 of the cylinder member 38 and/or the threads 286 of the camera adapter 28 could include an adhesive thereon for firmly connecting the cylinder member 38 to the camera adapter 28. When the camera adapter 28 is fully screwed onto the endoscope connector 26, the fourth O-ring 218 in the circumferential inner O-ring channel 216 in the proximal side smaller diameter area 214 of stepped interior surface 198 of the tube 194 of the zoom adjustment member 22 will abut against the exterior surface of the cylinder 16 of the cylinder member 38 in a radial direction, an end of the smaller diameter proximal second side portion 204 of the stepped exterior surface 196 of the tube 194 of the zoom adjustment member 22 will axially abut the zoom ring abutment step 282 in the stepped interior bore 274 of the externally threaded cylinder 262 of the camera adapter 28, the second O-ring 104 will axially abut the O-ring abutment step 284 in the stepped interior bore 274 of the externally threaded cylinder 262 of the camera adapter 28, and the proximal end 100 of the cylinder 16 will axially abut the inwardly extending disc-shaped flange 268 at the proximal end 100 of the externally threaded cylinder 262 of the camera adapter 28.

In the illustrated embodiment, circular movement of the zoom adjustment member 22 causes the zoom lens 18 to move axially within the cylinder 16 of the housing assembly 12. The zoom lens 18 is moved axially within the cylinder 16 by rotating the zoom adjustment member 22. As the zoom adjustment member 22 is rotated about the cylinder 16, the second threaded pin 192 will also rotate with the zoom adjustment member 22. As the second threaded pin 192 is rotated, the second threaded pin 192 will slide axially along the axial groove 220 in the proximal side smaller diameter area 214 of the stepped interior surface 198 of the tube 194 of the zoom adjustment member 22 and will also move along the zoom cut-out track 98 in the cylinder 16. Accordingly, the zoom lens holder assembly 160 connected to the second threaded pin 192 and with the zoom lens 18 therein will move axially along cylinder 16, thereby moving the zoom lens 18 either towards or away from the object being viewed to magnify the object.

Likewise, movement of the focus adjustment member 24 causes the focus lens 20 to move axially within the cylinder 16 of the housing assembly 12. The focus adjustment member 24 is moved by rotating the outer focus ring assembly 224, which will cause the second magnets 236 within the second magnet pockets 250 in the inner magnet band 238 to also rotate in a circular fashion. The magnetic force of the second magnets 236 will penetrate through the tube 194 of the zoom adjustment member 22 to interact with the first magnets 234 within the first magnet pockets 230 in the tube 226 of the inner magnet ring 222, thereby causing the inner magnet ring 222 to rotate when the outer focus ring assembly 224 is rotated. As the inner magnet ring 222 is rotated about the cylinder 16, the first threaded pin 158 will also rotate with the inner magnet ring 222. As the first threaded pin 158 is rotated, the first threaded pin 158 will slide axially along the inner axial groove 228 in the inner magnet ring 222 and will also move along the focus cut-out track 96 in the cylinder 16. Accordingly, the focus lens holder assembly 128 connected to the first threaded pin 158 and with the focus lens 20 therein will move axially along cylinder 16, thereby moving the focus lens 20 either towards or away from the object being viewed to focus the object.

In the illustrated example, the outer focus ring assembly 224 of the focus adjustment member 24 will rotate with rotation of the zoom adjustment member 22 (unless the outer focus ring assembly 224 is actively held stationary while the zoom adjustment member 22 is rotated). As illustrated in FIG. 3, the zoom adjustment member 22 is rotated relative to the cylinder 16 by overcoming a first frictional engagement between (1) the cylinder 16 and the fourth O-ring 218 in the circumferential inner O-ring channel 216 of the proximal side smaller diameter area 214 of the stepped interior surface 198 of the tube 194 of the zoom adjustment member 22 and (2) the inner surface of the distal side larger diameter area 212 of the stepped interior surface 198 of the tube 194 of the zoom adjustment member 22 and the first O-ring 94 in the O-ring track 93 of the cylinder member 38 of the endoscope connector 26. The outer focus ring assembly 224 is rotated relative to the zoom adjustment member 22 by overcoming a second frictional engagement between the third O-ring 208 in the O-ring groove 206 in the stepped exterior surface 196 of the tube 194 or the zoom adjustment member 22 and the smooth inner surface 242 of the inner magnet band 238 of the outer focus ring assembly 224 of the focus adjustment member 24. A first coefficient of friction at the first frictional engagement is greater than a second coefficient of friction at the second frictional engagement such that rotating the outer focus ring assembly 224 of the focus adjustment member 24 will not rotate the zoom adjustment member 22.

Accordingly, rotating the zoom adjustment member 22 will cause the image passing through the parfocal coupler 10 to have its magnification and its focus change (i.e., its image will magnify and the image plane will move along an axis of the coupler 10). However, rotating the outer focus ring assembly 224 of the focus adjustment member 24 will cause the image passing through the parfocal coupler 10 to have only its focus change (i.e., the image plane will move along an axis of the coupler 10). Therefore, using the parfocal coupler 10 as illustrated herein, one using the endoscopic viewing system 1 can adjust the magnification of the image and automatically adjust the focal plane of the image by adjusting only one knob or member. Therefore, the parfocal coupler 10 can be used with various cameras 14 having image planes at different locations along the central axis 5. Furthermore, the focus adjustment member 24 can be further adjusted to finely focus the image. Typically, the focus will only need to be adjusted if the endoscope 11 is moved closer or farther away from the object being viewed. In the illustrated embodiment, the fourth O-rings 218, the first O-ring 94, and the third O-ring 208 can be self-lubricating O-rings to ensure that the coefficients of friction remain constant before and after sterilization of the coupler 10.

It is to be understood that variations and modifications can be made on the aforementioned structure without departing from the concepts of the present invention. For example, it is contemplated that any of the parts of the coupler 10 can be manufactured in any manner, that most of the parts can be made using any materials (e.g., metal, elastomer or plastic) and that lenses can be made of any suitable material (e.g., glass or plastic). Furthermore, it is to be understood that such concepts are intended to be covered by the following claims unless these claims by their language expressly state otherwise.

We claim:

1. A coupler for connecting an endoscope to a camera, the coupler defining an axis and comprising:
   a housing assembly configured to be connected to a camera and an endoscope, the housing assembly including a cylinder mounting at least one zoom lens and at least one focus lens therein;
   a zoom adjustment member and a focus adjustment member located outside of the cylinder of the housing assembly, the zoom adjustment member engaging the cylinder with a first coefficient of friction and being movable relative thereto to cause axial movement of the at least one zoom lens within the cylinder of the housing assembly, the zoom adjustment member being operatively connected to the focus adjustment member such that movement of the zoom adjustment member causes the focus adjustment member to move thereby moving both the at least one zoom lens and the at least one focus lens axially within the cylinder, the focus adjustment member engaging the zoom adjustment member with a second coefficient of friction and being movable relative thereto to cause axial movement of the at least one focus lens within the cylinder of the housing assembly, the first coefficient of friction being greater than the second coefficient of friction such that movement of the focus adjustment member does not cause movement of the zoom adjustment member.

2. The coupler of claim 1, wherein:
   the zoom adjustment member comprises a zoom ring surrounding the cylinder of the housing assembly, wherein rotation of the zoom ring causes the at least one zoom lens to move axially within the cylinder of the housing assembly; and
   the focus adjustment member comprises a focus ring surrounding the cylinder of the housing assembly, wherein rotation of the focus ring causes the at least one focus lens to move axially within the cylinder of the housing assembly, and wherein rotation of the zoom ring causes the focus ring to rotate, thereby moving both the at least one zoom lens and the at least one focus ring axially within the cylinder, and rotation of the focus ring does not cause rotation of the zoom ring.

3. The coupler of claim 2, wherein:
   the at least one focus lens is positioned within a focus lens housing, and rotation of the focus ring causes the focus lens housing to rotate;
   the at least one zoom lens is positioned within a zoom lens housing, and rotation of the zoom ring causes the zoom lens housing to rotate.

4. The coupler of claim 3, wherein:
   the cylinder defines therein at least one non-linear zoom track and at least one non-linear focus track;
   the zoom lens housing includes a zoom extension extending into the at least one non-linear zoom track, with rotation of the zoom ring causing the zoom extension to slide along the at least one non-linear zoom track to move the zoom lens housing; and
   the focus lens housing includes a focus extension extending into the at least one non-linear focus track, with rotation of the focus ring causing the focus extension to slide along the at least one non-linear focus track to move the focus lens housing.

5. The coupler of claim 4, wherein the zoom ring includes a linear slot extending axially along an inner surface thereof and receiving a portion of the zoom extension such that rotation of the zoom ring causes the portion of the zoom extension within the linear slot to move along the linear slot.

6. The coupler of claim 4, wherein the focus ring includes a linear slot extending axially along an inner surface thereof and receiving a portion of the focus extension such that rotation of the focus ring causes the portion of the focus extension within the linear slot to move along the linear slot.

7. The coupler of claim 6 wherein:
   the focus ring includes an inner magnetic ring and an outer magnetic ring, the zoom ring being located between the inner magnetic ring and the outer magnetic ring such that the inner magnetic ring is separated from the outer magnetic ring;
   the inner magnetic ring includes the axial linear slot;
   the outer magnetic ring is magnetically coupled to the inner magnetic ring; and
   the outer magnetic ring surrounds a portion of the zoom ring and engages the zoom ring.

8. The coupler of claim 1, wherein:
   the at least one zoom lens comprises at least one zoom lens pair; and
   the at least one focus lens comprises at least one focus lens pair.

9. The coupler of claim 1, wherein the housing assembly includes an endoscope connector configured to receive an endoscope therein, the endoscope connector including retractable wedges movable relative to the cylinder, the retractable wedges allowing an endoscope to be selectively connected to and disconnected from the endoscope connector.

10. The coupler of claim 9, wherein the housing assembly includes a camera adapter configured to be threadingly engaged with a camera, the camera adapter being threadingly engaged with the endoscope connector.

11. A coupler for connecting an endoscope to a camera, the coupler defining an axis and comprising:

a housing configured to be connected to a camera and an endoscope, the housing having at least one zoom lens and at least one focus lens therein;

a zoom adjustment member located outside of the housing, the zoom adjustment member engaging the housing with a first coefficient of friction and being movable relative thereto to cause axial movement of the at least one zoom lens within the housing; and a focus adjustment member located outside of the housing, the focus adjustment member including an inner magnetic ring and an outer magnetic ring, the zoom adjustment member being located between the inner magnetic ring and the outer magnetic ring, the outer magnetic ring being magnetically coupled to the inner magnetic ring, the outer magnetic ring engaging the zoom adjustment member with a second coefficient of friction such that movement of the zoom adjustment member causes the outer magnetic ring to move thereby moving both the at least one zoom lens and the at least one focus lens within the housing;

the first coefficient of friction being greater than the second coefficient of friction such that movement of the outer magnetic ring does not cause movement of the zoom adjustment member.

12. The coupler of claim 11, wherein:
the at least one focus lens is positioned within a focus lens housing, and rotation of the focus ring causes the focus lens housing to rotate;
the at least one zoom lens is positioned within a zoom lens housing, and rotation of the zoom ring causes the zoom lens housing to rotate.

13. The coupler of claim 12, wherein:
the housing defines therein at least one non-linear zoom track and at least one non-linear focus track;
the zoom lens housing includes a zoom extension extending into the at least one non-linear zoom track, with rotation of the zoom adjustment member causing the zoom extension to slide along the at least one non-linear zoom track to move the zoom lens housing; and
the focus lens housing includes a focus extension extending into the at least one non-linear focus track, with rotation of the focus adjustment member causing the focus extension to slide along the at least one non-linear focus track to move the focus lens housing.

14. The coupler of claim 13, wherein the zoom adjustment member comprises a zoom ring having a linear slot extending axially along an inner surface thereof and receiving a portion of the zoom extension such that rotation of the zoom ring causes the portion of the zoom extension within the linear slot to move along the linear slot.

15. The coupler of claim 13, wherein the inner magnetic ring includes a linear slot extending axially along an inner surface thereof and receiving a portion of the focus extension such that rotation of the inner magnetic ring causes the portion of the focus extension within the linear slot to move along the linear slot.

16. The coupler of claim 11, wherein:
the at least one zoom lens comprises at least one zoom lens pair; and
the at least one focus lens comprises at least one focus lens pair.

17. The coupler of claim 11, wherein the housing includes an endoscope connector configured to receive an endoscope therein, the endoscope connector including movable and retractable wedges, the movable and retractable wedges allowing an endoscope to be selectively connected to and disconnected from the endoscope connector.

18. The coupler of claim 17, wherein the housing includes a camera adapter configured to be threadingly engaged with a camera, the camera adapter being threadingly engaged with the endoscope connector.

19. A coupler for connecting an endoscope to a camera, the coupler defining an axis and comprising:
a housing assembly configured to be connected to a camera and an endoscope, the housing assembly including a cylinder having at least one zoom lens pair and at least one focus lens pair therein, with the at least one zoom lens pair and the at least one focus lens pair being configured to slide axially within the cylinder;

a zoom ring member located outside of the cylinder of the housing assembly and engaging the cylinder of the housing assembly with a first coefficient of friction, the zoom ring member being rotatable about the cylinder of the housing assembly to cause axial movement of the at least one zoom lens pair within the cylinder of the housing assembly; and a focus adjustment member located outside of the cylinder of the housing assembly, the focus adjustment member including an inner magnetic ring and an outer magnetic ring, the zoom ring member being located between the inner magnetic ring and the outer magnetic ring such that the inner magnetic ring is separated from the outer magnetic ring, the inner magnetic ring being mechanically connected to the at least one focus lens pair, the outer magnetic ring being magnetically coupled to the inner magnetic ring, the outer magnetic ring surrounding a portion of the zoom ring member and engaging the zoom ring member with a second coefficient of friction, the outer magnetic ring being carried on the zoom adjustment ring such that rotation of the zoom ring member causes the outer magnetic ring to rotate thereby moving both the at least one zoom lens pair and the at least one focus lens pair axially within the cylinder of the housing assembly, the first coefficient of friction being greater than the second coefficient of friction such that movement of the outer magnetic ring does not cause movement of the zoom ring member such that the at least one focus lens pair will move axially within the cylinder of the housing assembly without the at least one zoom lens pair moving axially within the cylinder of the housing assembly.

20. The coupler of claim 19, further including:
a focus lens housing having the at least one focus lens pair therein; and
a zoom lens housing having the at least one zoom lens pair therein.

21. The coupler of claim 20, wherein:
the cylinder defines therein at least one non-linear zoom track and at least one non-linear focus track;
the zoom lens housing includes a zoom extension extending into the at least one non-linear zoom track, with rotation of the zoom ring member causing the zoom extension to slide along the at least one non-linear zoom track to move the zoom lens housing; and
the focus lens housing includes a focus extension extending into the at least one non-linear focus track, with rotation of the focus adjustment member causing the focus extension to slide along the at least one non-linear focus track to move the focus lens housing.

22. The coupler of claim 21, wherein the zoom ring member has a linear slot extending axially along an inner surface thereof and receiving a portion of the zoom extension such that rotation of the zoom ring member causes the portion of the zoom extension within the linear slot to move along the linear slot.

23. The coupler of claim 21, wherein the inner magnetic ring includes a linear slot extending axially along an inner surface thereof and receiving a portion of the focus extension such that rotation of the inner magnetic ring causes the portion of the focus extension within the linear slot to move along the linear slot.

24. The coupler of claim 21, wherein the housing includes an endoscope connector configured to receive an endoscope therein, the endoscope connector including movable and retractable wedges, the movable and retractable wedges allowing an endoscope to be selectively connected to and disconnected from the endoscope connector.

25. The coupler of claim 24, wherein the housing assembly includes a camera adapter configured to be threadingly engaged with a camera, the camera adapter being threadingly engaged with the endoscope connector.

* * * * *